United States Patent
Salisbury et al.

(10) Patent No.: US 11,827,870 B2
(45) Date of Patent: Nov. 28, 2023

(54) DEVICE FOR PRODUCING METABOLITES

(71) Applicant: Generen Labs, Inc., Austin, TX (US)

(72) Inventors: Markos Aurelio Salisbury, Austin, TX (US); Robert Allen Ersek, Austin, TX (US)

(73) Assignee: Generen Labs, Inc., Austin, TX (US)

( * ) Notice: Subject to any disclaimer, the term of this patent is extended or adjusted under 35 U.S.C. 154(b) by 0 days.

(21) Appl. No.: 17/669,290

(22) Filed: Feb. 10, 2022

(65) Prior Publication Data

US 2022/0372416 A1 Nov. 24, 2022

Related U.S. Application Data

(60) Provisional application No. 63/191,234, filed on May 20, 2021.

(51) Int. Cl.
| | | |
|---|---|---|
| *C12M 1/12* | (2006.01) | |
| *C12M 1/00* | (2006.01) | |
| *C12M 1/06* | (2006.01) | |
| *C12M 1/34* | (2006.01) | |
| *C12M 1/26* | (2006.01) | |

(52) U.S. Cl.
CPC ............ *C12M 23/06* (2013.01); *C12M 23/26* (2013.01); *C12M 23/34* (2013.01); *C12M 27/02* (2013.01); *C12M 29/04* (2013.01); *C12M 33/14* (2013.01); *C12M 41/06* (2013.01); *C12M 41/12* (2013.01); *C12M 41/42* (2013.01)

(58) Field of Classification Search
CPC ...... C12M 23/06; C12M 23/26; C12M 23/34; C12M 27/02; C12M 29/04; C12M 33/14; C12M 41/06; C12M 41/12; C12M 41/42

USPC ...................................................... 435/289.1
See application file for complete search history.

(56) References Cited

U.S. PATENT DOCUMENTS

| | | | |
|---|---|---|---|
| 2,996,429 A * | 8/1961 | Toulmin, Jr. ........... | C12M 21/08 |
| | | | 435/298.2 |
| 4,043,903 A * | 8/1977 | Dor ......................... | C12M 41/06 |
| | | | 435/297.5 |
| 6,942,998 B1 | 9/2005 | Ooteghem | |
| 7,176,005 B2 | 2/2007 | Melis et al. | |
| 7,709,113 B2 | 5/2010 | Logan et al. | |
| 8,334,121 B2 * | 12/2012 | Schindler ........... | B01D 39/1623 |
| | | | 435/320.1 |
| 9,447,508 B2 | 9/2016 | Yoshida et al. | |
| 10,160,980 B2 | 12/2018 | Yang et al. | |
| 2012/0329089 A1 | 12/2012 | Edrei | |
| 2021/0002597 A1 * | 1/2021 | Jaques .................. | B01F 27/191 |
| 2021/0371793 A1 * | 12/2021 | Galliher ................ | C12M 23/26 |

FOREIGN PATENT DOCUMENTS

| | | | | |
|---|---|---|---|---|
| JP | 03238100 A | * | 10/1991 | ............ C12M 21/04 |

* cited by examiner

*Primary Examiner* — William H. Beisner
(74) *Attorney, Agent, or Firm* — Orrick, Herrington & Sutcliffe LLP

(57) ABSTRACT

A bioreactor for producing hydrogen gas and other metabolites. The bioreactor utilizes light, fermentation, and other metabolic processes for the production of metabolites, derived from various microorganisms contained within the bioreactor through respective metabolic pathways. The bioreactor comprises a main reactor chamber, a semipermeable membrane, a sleeve, a power supply, a substrate medium, a heating member, a plurality of tubing members, a collection reservoir, a pressure-sealed connecter member, and an agitator.

9 Claims, 7 Drawing Sheets

DEVICE FOR PRODUCING METABOLITES

FIELD OF THE INVENTION

The present invention relates generally to a metabolite-producing device and system. More specifically, the present invention is a device and system for producing metabolites, through a semipermeable membrane containing microorganisms activated by either or both a substrate and light.

BACKGROUND OF THE INVENTION

Hydrogen is the most abundant element in the known universe. Surprisingly, as common as hydrogen is, its gaseous state is not readily accessible to us without some human ingenuity. Common methods for producing hydrogen in its gaseous state include Natural Gas Reforming, or Gasification, Electrolysis, Renewable Liquid Reforming, and the Light-Bacteria-Direct Metabolic Process. Of these methods, Natural Gas Reforming, or Gasification, is the most affordable, common, and efficient, under typical conditions. However, Natural Gas Reforming relies on reacting natural gas with high-temperature steam. Although effective, this requires the mining or fracking of natural gas, a finite resource, and can be disruptive and potentially harmful to the environment. Electrolysis is another process of hydrogen gas production where water molecules are split by a strong electrical current to produce hydrogen gas and Oxygen. Electrolysis is only considered to be efficient if the large amount of electricity required for the reaction is sourced from renewable power sources, such as wind, solar, geothermal and hydroelectric, which can seldom produce enough power for the reaction. Renewable Liquid Reforming involves reacting renewable liquid fuels, such as ethanol, with steam to produce hydrogen gas. The cost of the biomass derived renewable liquid fuels is too great to be an efficient option at this time. The capital equipment costs, operation and maintenance costs, and processing inefficiency, make Renewable Liquid Reforming too inefficient of an option for practical and large-scale hydrogen gas production. The Light-Bacteria-Direct metabolic process involves the conversion of biomass into sugar-rich free stocks which can later be converted into hydrogen gas. Currently, hydrogen gas yield rates are too low to make this method a viable option for commercial production of hydrogen gas. One of the issues plaguing this method is the current bioreactor design, which cannot be run or replenished without disturbing or removing the microorganisms in the reactor. Another issue is that effective bioreactor designs cannot be scaled up to produce hydrogen gas on a commercial scale. The bioreactor device and system described herein provides solutions to both of these problems. The present invention is an efficient bioreactor that utilizes the Light-Bacteria-Direct metabolic production of hydrogen gas and other metabolites, derived from various microorganisms contained within the bioreactor through respective metabolic pathways.

DETAIL DESCRIPTIONS OF THE INVENTION

All illustrations of the drawings are for the purpose of describing selected versions of the present invention and are not intended to limit the scope of the present invention.

Figure 1:
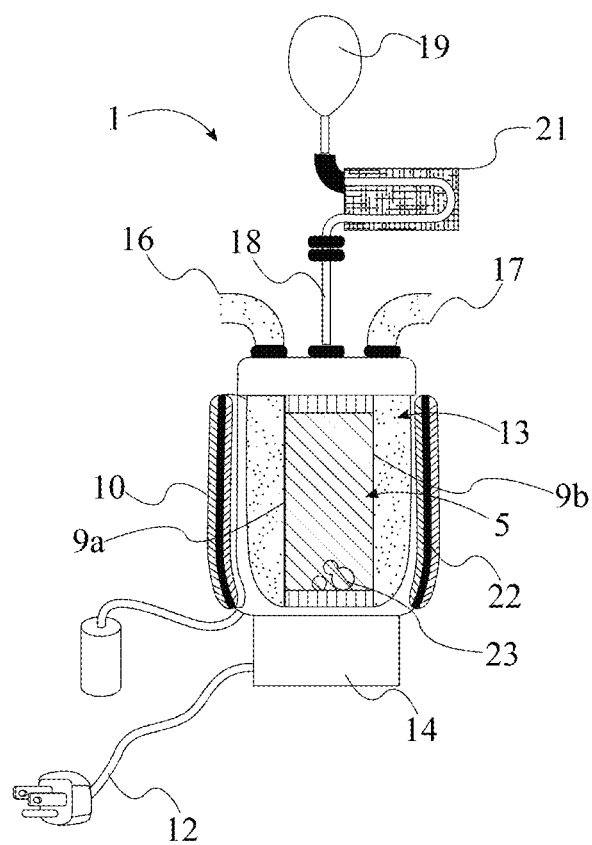
FIG. 1 shows a front cross-sectional view of an embodiment of the present invention.
Figure 2:
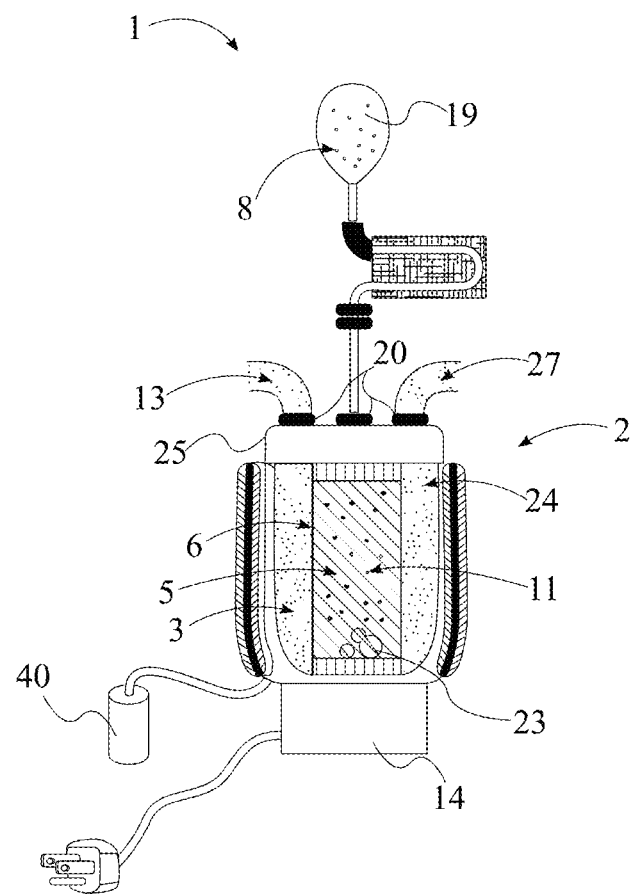
FIG. 2 shows a front cross-sectional view of an embodiment of the present invention with microorganisms and metabolites therein.

FIGS. 1-2 show a front cross-sectional view of an embodiment of the present invention. The present invention described herein is a bioreactor which produces metabolites 8, from the processing of a substrate medium 13, such as glucose and deionized water, by microorganisms 11, such as cyanobacteria. The bioreactor 1 comprises a main reactor chamber 2, including a substrate containment space 3; a semipermeable membrane 9a, 9b with a hollow inner lumen side 5, an external surface side 6; a sleeve 10 perimetrically enveloped around the main reactor chamber 2; microorganism 11, such as cyanobacteria, for producing metabolites 8; a power supply 12, preferably supplying energy derived from renewable sources; a substrate medium 13, such as glucose and deionized H2O; a heating member 14, such as a hotplate; a plurality of tubing members 15, comprising an inlet tubing member 16, an outlet tubing member 17, and a collection tubing member 18; a collection reservoir 19; a pressure-sealed connecter member 20; an agitator 23, such as a magnetic stirrer; and, a dial 26. The pressure-sealed connecter member 20 is hermetically sealed to the main reactor chamber 2, opposite the heating member 14 and agitator 23. The plurality of tubing members 15 are hermetically sealed and traverse through the pressure-sealed connecter member 20 to enter the substrate containment space 3 and the hollow inner lumen space 5 of the semipermeable membrane 9a, 9b. The semipermeable member 9a, 9b is housed within the main reactor chamber 2 within the substrate containment space 3. The substrate medium 13 fills the substrate containment space 3 by traveling through the inlet tubing member 16 into the substrate containment space 3. The substrate medium 13 envelopes the external surface side 6 of the semipermeable membrane 9a, 9b and diffuses across the concentration gradient through the semipermeable membrane 9a, 9b to fill the hollow inner lumen side 5. The microorganisms 11 are positioned within the semipermeable membrane 9a, 9b. The microorganisms 11 and substrate medium 13 within the hollow inner lumen side 5 of the semipermeable membrane 9a, 9b are then agitated. The agitated microorganisms 11 float in a homogenous mixture and are incapable of permeating through the semipermeable membrane 9a, 9b and into the substrate containment space 3. Metabolite 8 production is then stimulated from the microorganisms 11 within the hollow inner lumen space 5 of the semipermeable membrane 9a, 9b. The resulting unfiltered metabolites 24 escape the hollow inner lumen space 5 of the semipermeable membrane 9a, 9b through the collection tubing member 18 and by permeating through the semipermeable membrane 9a, 9b. The unfiltered metabolites 24 in a gaseous state will traverse through the collection tubing member 18 and are collected and stored in the collection reservoir 19, such as a rubber balloon. Any unfiltered biproducts 27 from the reaction that permeated through the semipermeable membrane 9a, 9b and entered the substrate containment space 3 are expelled from the main reactor chamber 2 through the outlet tubing member 17 and are collected, recycled, or responsibly disposed of.

In an alternative embodiment of the present invention a metabolite purifying filter member 21, such as a calcium bicarbonate filter, is attached adjacent the collection tubing member 18. When the gaseous metabolites 8 traverse through the collection tubing member 18 then will pass through the purifying filter member 21 and the desired metabolites will be separated from the precipitate.

In an alternative embodiment of the present invention a light source 22, such as light-emitting diodes (LED) at an optimal wavelength, is affixed within the sleeve 10. When activated, the light source 22 emits light into the substrate containment space 3 and penetrates the hollow inner lumen side 5 of the semipermeable membrane 9a, 9b, thereby, facilitating metabolite 8 production.

In another embodiment of the present invention a dial 26 is affixed to the heating member 14 and agitator 23. When the dial 26 is manipulated, it controls the speed of the agitator 23 which operates to mix the microorganisms 11 and substrate medium 13 within the hollow inner lumen side 5 of the semipermeable membrane 9a, 9b.

The substrate medium 13 is supplied to the main reactor chamber 2 of the bioreactor 1 at a predefined frequency—dependent on various factors such as the type of organism, the size of the bioreactor, volume of substrate medium desired, and pressure in the system—to permeate through the semipermeable membrane 9a, 9b and provide the microorganisms 11 with a consistent influx of necessary substrate medium 13 to facilitate the production of desired metabolites 8 without disrupting or removing the microorganisms 11 from the hollow inner lumen space 5 of the semipermeable membrane 9a, 9b. Further, the heating member 14, positioned opposite the pressure-sealed connecter member 20 and within the hollow inner lumen side 5, maintains a consistent, predefined temperature to maintain a predefined substrate medium temperature. A preferred temperature for the system is 40 F-140 F but can vary dependent on external and internal factors. Further, the agitator 23, positioned opposite the pressure-sealed connecter member 20 and within the hollow inner lumen side 5, maintains a consistent, predefined cyclical rate to maintain a homogenous mixture of substrate medium 13 and microorganism 11 within the hollow inner lumen side 5 of the semipermeable membrane 9a, 9b.

This device and system allows the microorganisms 11 to be supplied with an enriched substrate medium 13, without disturbing or removing the microorganisms 11 from the main reactor chamber 1, thereby facilitating continuous substrate medium 13 processing and metabolite 8 synthesis by the microorganisms 11 contained in the semipermeable membrane 9a, 9b. The type of microorganisms can vary from light-dependent bacteria like cyanobacteria to various algae. Alternatively, a direct metabolic pathway, such as fermentation, can be used in this system as well.

Commercial production of hydrogen gas and other metabolites by microorganisms in the device and system described herein is possible. Thus, it is important to note that changing small factors like adding modular fitting in order to chain them in a series does not change or improve upon the spirit of the invention described herein.

Figure 3:
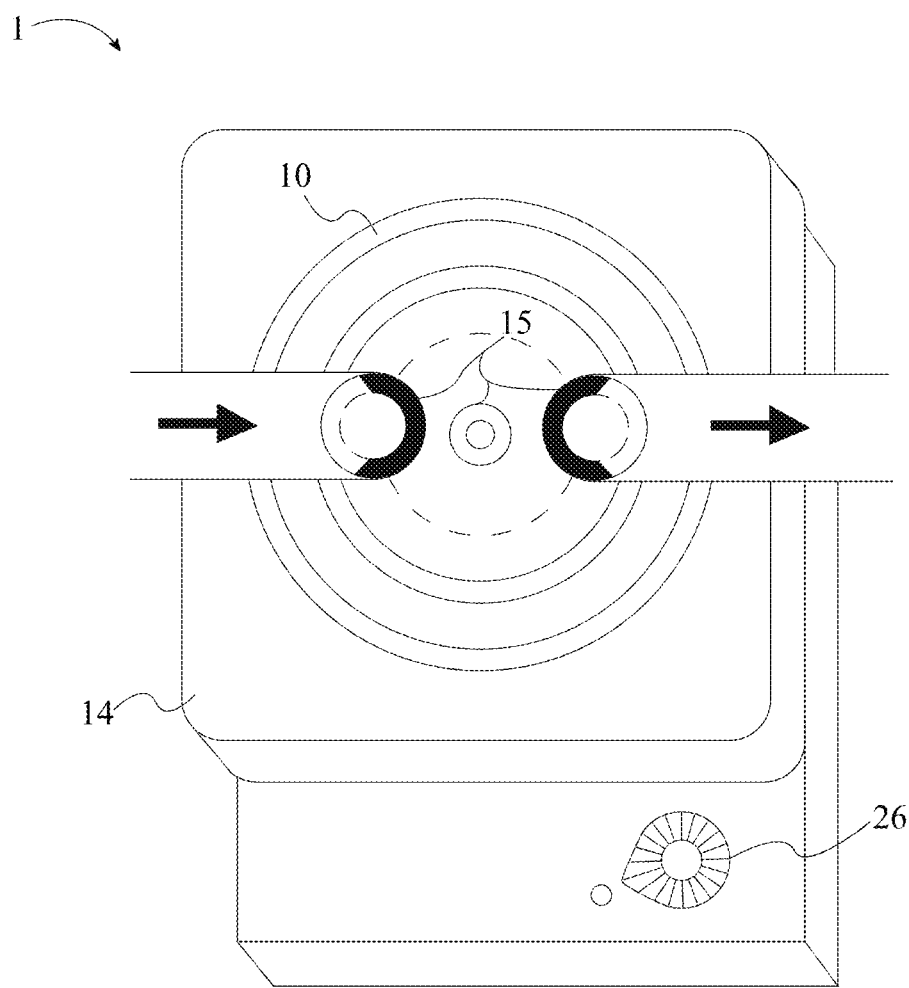
FIG. 3 shows a top plan view of an embodiment of the present invention.

FIG. 3 shows a top plan view of an embodiment of the present invention.

Figure 4:
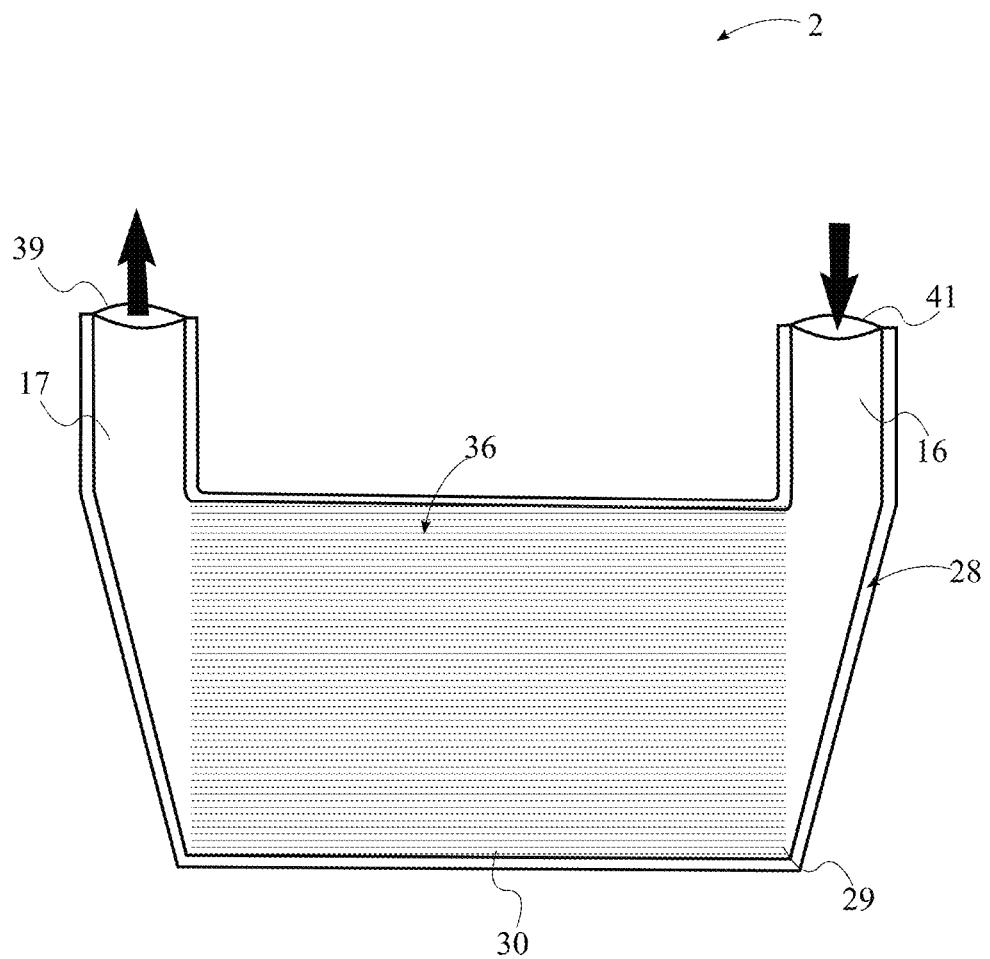
FIG. 4 shows an alternative embodiment of the present invention.

FIG. 4 shows an alternative embodiment of the present invention wherein the semipermeable membrane 9a, 9b contains at least two capillary membranes 29, preferably silicone rubber or cellulose, within a capillary bed 36. The alternative embodiment further comprises at least one capillary channel 30 between the at least two capillary membranes 29; connecting segments 31, wherein the at least two capillary membranes 29 are welded together by an outline border of double welding, adjoining the at least two capillary membranes 29 and enclosing the at least one capillary channel 30 within the at least two capillary membranes 29; a pulsation source 32, such as a peristalsis pump; a plurality of tubing members 15, comprising an inlet tubing member 16 and an outlet tubing member 17; and a pressure-sealed connecter member 20.

In this alternative embodiment the plurality of tubing members 15 are hermetically sealed and fashioned at opposite ends of the main reactor chamber 2. The at least two capillary membranes 29 are housed within the capillary bed 36 between the inlet tubing member 16 and outlet tubing member 17. The at least two capillary membranes 29 are fashioned into parallel rows and the substrate medium then fills the at least one capillary channel 30 by traveling through the inlet tubing member 16 via forces exerted from the pulsation source 32, which is hermetically sealed and attached adjacent the inlet tubing member 16, opposite the at least two capillary membranes 29. The substrate medium 13 envelopes the at least two capillary membranes 29 and permeates through the at least one capillary channel 30. The microorganisms 11 within the system are positioned within the substrate medium 13 and the at least two capillary membranes 29 in a homogenous mixture. The unfiltered metabolites 8 produced from the microorganisms traverse through the outlet tubing member and are collected in a collection reservoir 19.

Figure 5:
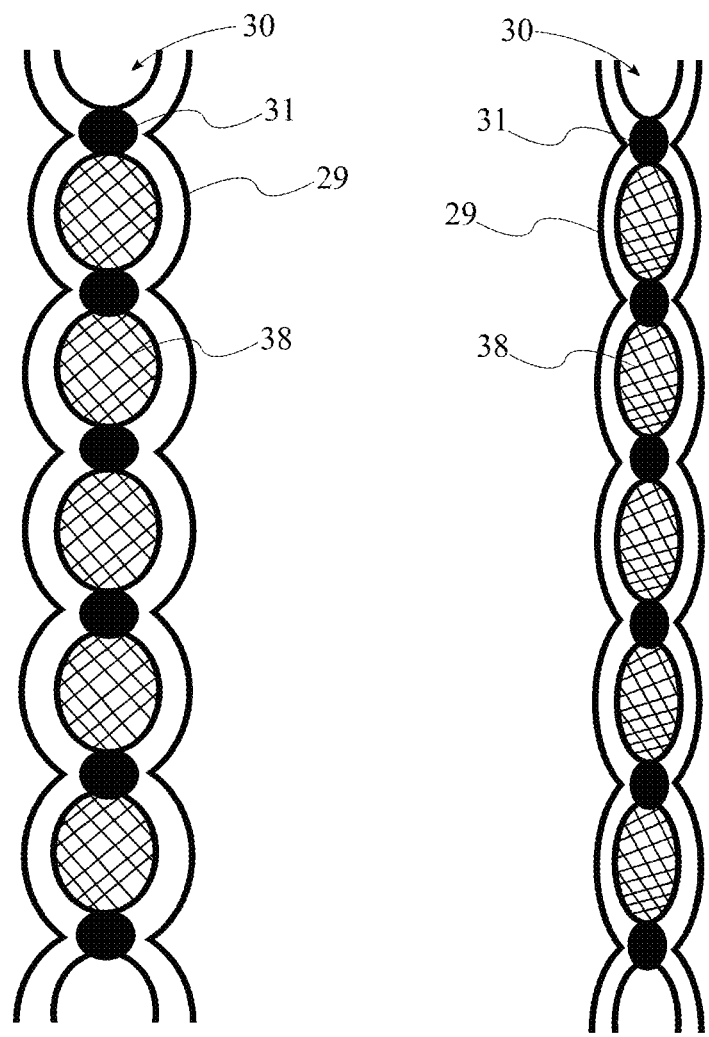
FIG. 5 shows an exploded, cross-sectional right side view of capillary membranes and channels of an alternative embodiment of the present invention in variable low- and high-internal pressure environments.

FIG. 5 shows an exploded, cross-sectional right side view of capillary membranes and channels of an alternative embodiment of the present invention in high and low pressure, internal or external of the membrane. Namely, the exploded view shows the at least two capillary membranes 29, at least one capillary channel 30, and the connecting segments 31 in greater detail.

Figure 6:
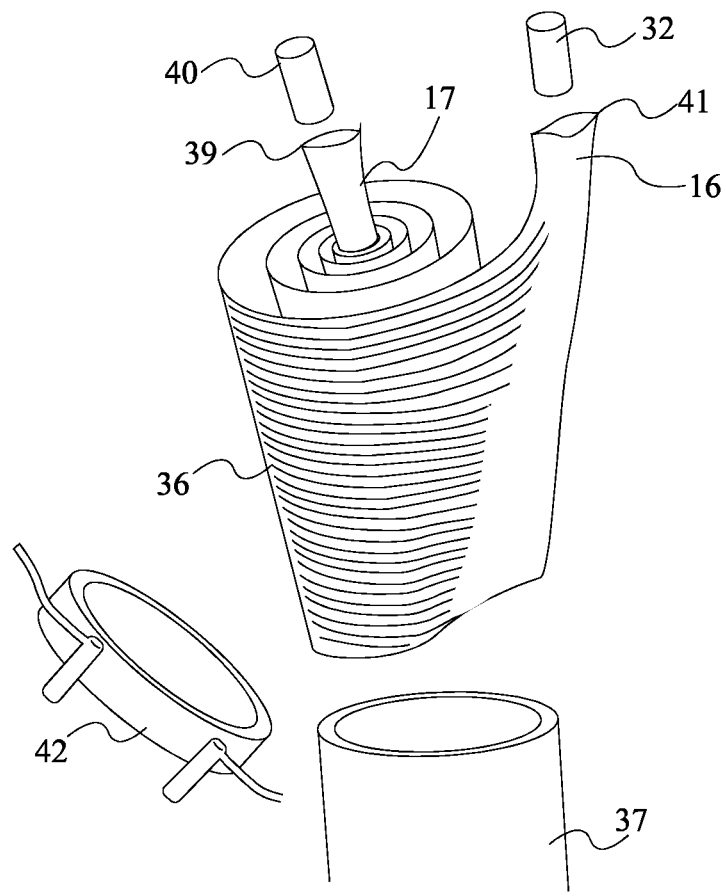
FIG. 6 shows an alternative embodiment of the present invention wherein the semipermeable membrane is in a rolled-up configuration.

FIG. 6 shows an alternative embodiment of the present invention wherein the semipermeable membrane 9a, 9b with at least two capillary membranes 29 within a capillary bed 36 is in a rolled-up configuration, or positioned cylindrically around the outlet tubing member in multiple layers with space between the layers, with nylon or Dacron scrim 38 between the layers of the semipermeable membrane 9a, 9b to prevent the surfaces of the semipermeable 9a, 9b membrane in the rolled-up configuration from being juxtaposed; and the inert scrim being of a net configuration so gases or nutrients flow freely through the fenestrations and allow the full surface of the semipermeable membrane 9a, 9b to be separated from each other. This rolled-up configuration is then placed within a canister 37, made of a rigid inert material such as glass or methyl methacrylate, or a more flexible but semi rigid material such as polypropylene, and has a cap member 42.

The inlet tubing member 16 passes through the capillary bed 36 and exits through an exit port 39 to the collection reservoir 19. The canister 37 is semi-ridged and houses the entire system. The canister has an inflow controlled by a pressure source 40, such as an air pump or vacuum, so that inflow and outflow of the homogenous mixture of microorganism 11 and metabolites 8 can be regulated to add sufficient pressure to the membrane by either including it or opening it for flow.

UNEXPECTED RESULTS

Figure 7:
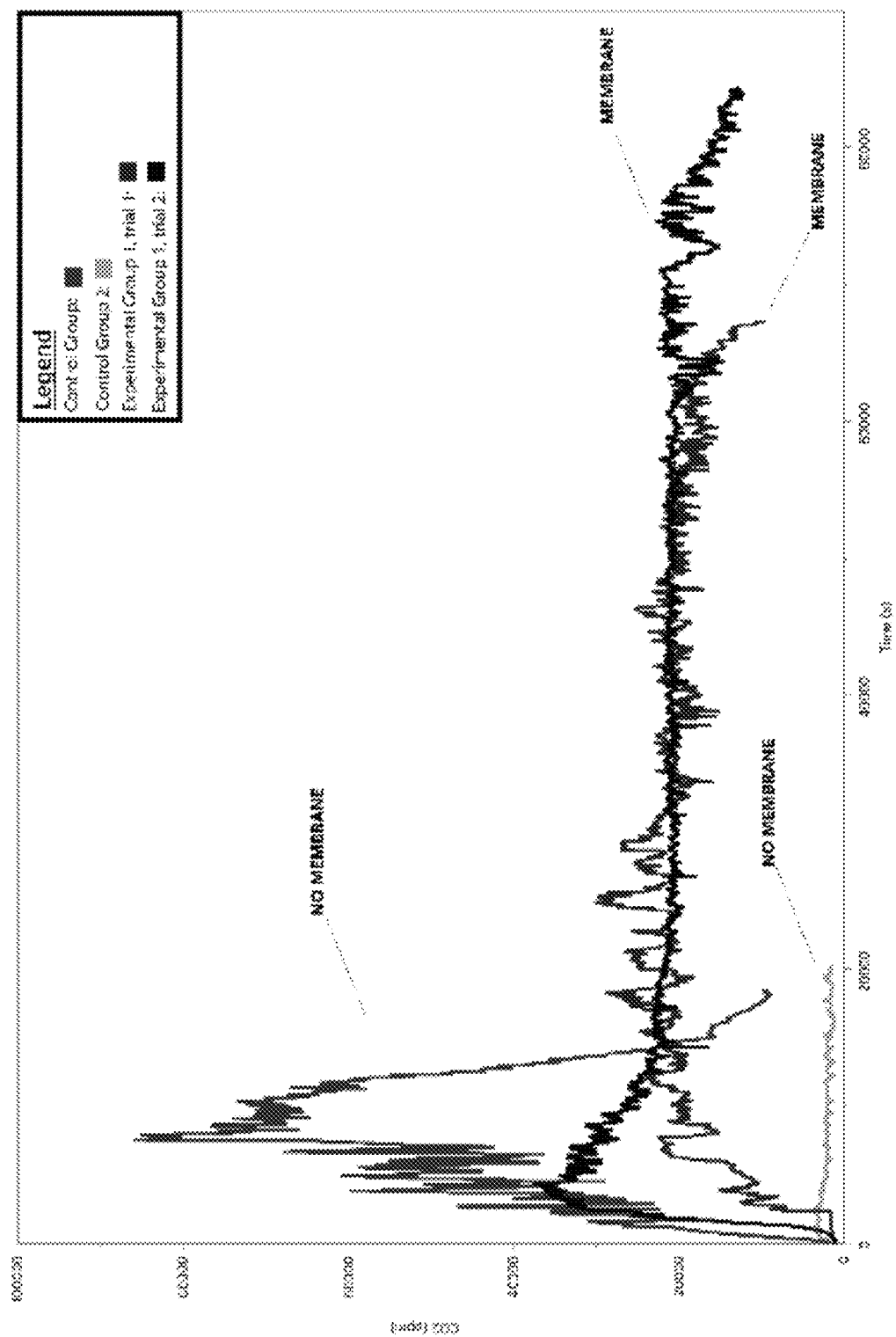
FIG. 7 shows a chart illustrating the results of an experiment showing production curves and metabolic calculations of nutrient consumption by yeast in an embodiment of the present invention.

For the experiment depicted in FIG. 7, instant yeast was used as the microorganism and sugar water was used as the nutrient mix. The proportions of the mixtures are 12 parts water, 1 part sugar and 0.25 parts yeast. Yeast was chosen because of its availability, safety, speed of reaction, and its generalizability to other fermentative microorganisms. The results of these experiments are generalizable to other microorganisms. This experiment evaluated three different experimental conditions: two control groups, one where no membrane was used, and another one where no membrane is used, but the same amount of yeast as the other cases is used but mixed with the same amount of sugar water as the first control group, to test for comparable production and efficiency; and an experimental group where the yeast are contained in the membrane and submerged in a nutrient medium. All these groups used the same amount of yeast in 35 ml of water. Each trial had a 3 mm gap at the sensor to allow for the $CO_2$ to vent out.

Control:

In the control group 0.7 g of instant yeast was mixed with 35 ml water in the reactor bottle then placed it on a hotplate set to 60 degrees Celsius. Once the mixture was at temperature, the 3 g of sugar was poured in, and the sensor cap was placed on the bottle with skewers creating a 3 mm space between the cap and bottle so the $CO_2$ could vent out of the bioreactor. Once assembled, logger software was started, and $CO_2$ readings were taken every 4 seconds in units of parts per million. After $CO_2$ production fell to an inactive level, the reaction was stopped.

Control Group 2 (No Membrane):

For the second control group, a test was conducted to determine what would happen if the same 0.7 g of yeast was mixed with 30 g of sugar and 350 ml of water, just as in the first experimental group, but without a membrane. This was testing whether mixing the same amount of yeast with more nutrient mix would yield comparable levels of production to the two trials in experimental group 1. 0.7 grams of instant yeast was mixed with 350 ml water in the bioreactor bottle then placed on a hotplate set to 60 degrees Celsius. Once the mixture was at temperature, the 30 g of sugar was poured in, and the sensor cap was placed on the bottle with skewers. Once assembled, the logger software was started, and $CO_2$ readings were taken every 4 seconds in units of parts per million. After the $CO_2$ production fell to an inactive level, the reaction was stopped.

Group 1:

In the first experimental group, the membrane was fixed in the reactor with a spacer to raise the reactor opening, so the membrane could hang down without touching the bottom. Another spacer was then used to secure the sensor above the membrane opening. The membrane was fixed in between these two spacers. The membrane tubing was sealed at one end and secured to a 1" piece of tubing at its opening, which was then passed through 6"×6" square of layered cellophane wrap so that the membrane could hang in between the two spacers like an eardrum or diaphragm. Once the assembly was made, the reactor bottle was filled with 350 ml of water and mixed in 30 g of table sugar, then placed on a hotplate set to 60 degrees Celsius for the substrate medium to heat up. In the meantime, the membrane was prepared and filled with 35 ml water (like the control), to which the 0.7 g of yeast was mixed in. Once the membrane mixture was prepared, the bioreactor bottle was assembled with spacers and a membrane, and the $CO_2$ sensor was placed at the top. After assembly the logging software was started, which took $CO_2$ readings every 4 seconds, in parts per million. After the $CO_2$ production fell to an inactive level, the reaction was stopped. This experimental group was run twice and is identifiable on FIG. 7 by its labeling as "membrane."

Findings and Discussion:

As FIG. 7 clearly illustrates, there were dramatic, unexpected results that came from the experiments. The control group had a very typical production curve that followed a normal distribution. Additionally, the control group had a strong rise at the beginning of the trial that peaked at approximately 83,000 ppm and then swiftly fell off to below 10,000 ppm. The reaction ran for a total of 19,000 seconds and ended up consuming under 3 g of sugar.

The second control group was prepared like the first control group but with 350 ml of water and 30 g of sugar instead. The second control group was intended to demonstrate that even with more nutrient mix, the 0.7 g of yeast would be no more productive than the control. Ultimately, it was determined that the second control group could not compete with the first control group. The trial never reached a production level higher than 3050 ppm and was recorded to have stopped at just over 20,000 seconds, though it probably could have been stopped sooner.

The experimental group had two trials. In the first trial, the production curve started out flat because, when mixed, the yeast and water in the membrane did not have any added sugars. For the reaction to take place, enough sugars would need to enter the inner membrane space to cross the reaction's activation threshold, meaning that any significant $CO_2$ production would clearly indicate the membrane allowed sugars to permeate and mix in with the yeast. After the activation threshold was crossed at approximately 4,500 seconds, there was a swift climb up to nearly 23,000 ppm. The production levels stayed in a range of 22,000 ppm to 25,000 ppm during the peak of the reaction, which was nearly 50,000 seconds. Slowly, the productivity began to decrease, and the reaction was recorded to have ended at 68,000 seconds. The experiment was repeated for the second trial, however the same membrane was used for the second trial that was used in the first trial, to show system resiliency. Surprisingly, the second trial did not have the same initial period of low to no productivity and ran for a longer duration than the first trial. There was an almost immediate rise to nearly 40,000 ppm from where it dropped to a constant production level right above 22,000 ppm that it carried for about 76,000 seconds, at which point the productivity fell off and the reaction was recorded to have ended at just under 85,000 seconds. The two trials both ran for about four times the duration as the control group and demonstrated how the bioreactor with a membrane can create an environment for microorganisms that allows for continuous metabolism.

One question raised by these experimental results was: why are the first experimental group curves so much lower than the first control group? Right away the area under the curves can make it appear that the control group may have a greater or comparable total $CO_2$ production to the first experimental group. To investigate this, the fluid left over in the container from the second trial of the first experimental group was collected and distilled to separate the water and ethanol from the remaining sugars and any other particulates. After distilling, 330 ml ethanol-water solution was left. This distilled liquid was then taken and tested using an ethanol by volume meter. With this meter, it was determined that the second trial of the first experimental group produced a solution that was 3.5% ethanol by volume, meaning approximately 11.55 ml of pure ethanol was produced. Now that the amount of ethanol produced was determined, some metabolic calculations were performed to extrapolate how much sugar was consumed. The calculations revealed that the second trial was able to consume nearly 19 g of sugar, which is over six times the maximum amount of sugar the 0.7 g of yeast could have consumed in the control, and many times greater than the sugar consumed in the second experimental group. These findings were unexpected and showed that a bioreactor with a membrane facilitated increased nutrient consumption by yeast as opposed to a bioreactor without the membrane.

CONCLUSION

As shown by both the production curves and the metabolic calculations in FIG. 7, the bioreactor with a membrane was able to both extend the duration of metabolism and increase the total consumption potential of nutrients per mg of yeast. This means that one can get the same amount of production out of 0.7 g of yeast that one could expect to get out of approximately 7 g of yeast (following the mixture proportion previously mentioned). Further, it requires fewer nutrient inputs to get the same if not greater total production of metabolites when using our semipermeable membrane process to isolate the microorganisms. Further, these results demonstrate how the implementation of the membrane in tank bioreactors creates a more efficient system that requires less nutrients, less energy, less maintenance and produces less waste products. Finally, the simplicity of this system means that it is straightforward to run many reactors or colonies of microorganisms in an array that produces an industrial level of metabolic byproducts.

Although the invention has been explained in relation to its preferred embodiment, it is to be understood that many other possible modifications and variations obvious to anyone familiar with the art can be made without departing from the spirit and scope of the invention.

What is claimed is:
1. A bioreactor comprising:
a main reactor chamber, including a substrate containment space;
a semipermeable membrane with a hollow inner lumen side and an external surface side;
a sleeve perimetrically enveloped around the main reactor chamber;
an electric power supply;
a substrate medium;
a heating member;
a plurality of tubing members;
a collection reservoir;
a pressure-sealed connecter member;
a metabolite purifying filter member;
an agitator;
the plurality of tubing members comprising an inlet tubing member and a collection tubing member;
the pressure-sealed connecter member hermetically sealed to the main reactor chamber, opposite the heating member and the agitator;
the substrate medium fills the substrate containment space by traveling through the inlet tubing member into the substrate containment space;
the substrate medium envelopes the external surface side of the semipermeable membrane and permeates through the semipermeable membrane to fill the inner lumen side;
the heating member maintains a predefined temperature to maintain a predefined substrate temperature;
the agitator maintains a predefined cyclical rate;
the electric power supply coupled to the heating member;
the collection tubing member traverses through the pressure-sealed connector member to enter the hollow inner lumen space of the semipermeable membrane;
the metabolite purifying filter member connected to the semipermeable membrane by the collection tubing member of the plurality of tubing members; and
the collection reservoir connected to the metabolite purifying filter member by the collection tubing member.
2. The bioreactor of claim 1, wherein the semipermeable member is housed within the main reactor chamber within the substrate containment space.
3. The bioreactor of claim 1, wherein
the plurality of tubing members further comprises an outlet tubing member;
the plurality of tubing members are hermetically sealed to the pressure-sealed connecter member;
the inlet tubing member and outlet tubing member traverse through the pressure-sealed connecter member to enter the substrate containment space; and
the collection tubing member traverses through the pressure-sealed connecter member to enter the hollow inner lumen space of the semipermeable membrane.
4. The bioreactor of claim 3, further comprising:
a light source;
the light source contained within the sleeve; and
the light source having a variable wavelength, wherein the wavelength is varied to promote metabolite production by a plurality of microorganisms contained within the hollow lumen space of the semipermeable membrane.
5. The bioreactor of claim 3, wherein the substrate medium is supplied to the substrate containment space at a predefined flow rate to permeate through the semipermeable membrane and into the hollow inner lumen space without disrupting or removing the contents therein.
6. The bioreactor of claim 5, wherein a dial increases or decreases the temperature of the heating member and cyclical rate of the agitator.
7. A bioreactor comprising:
a main reactor chamber, including a substrate containment space;
a semipermeable membrane with a hollow inner lumen side and an external surface side;
a sleeve perimetrically enveloped around the main reactor chamber;
an electric power supply;
a substrate medium;
a heating member;
a plurality of tubing members;
a collection reservoir;
a pressure-sealed connecter member;
a metabolite purifying filter member;
an agitator;
the pressure-sealed connecter member hermetically sealed to the main reactor chamber, opposite the heating member and the agitator;
the semipermeable membrane is housed within the main reactor chamber within the substrate containment space;

the plurality of tubing members includes an inlet tubing member, an outlet tubing member, and a collection tubing member;

the plurality of tubing members are hermetically sealed to the pressure-sealed connecter member;

the inlet tubing member and outlet tubing member traverse through the pressure-sealed connecter member to enter the substrate containment space;

the collection tubing member traverses through the pressure-sealed connecter member to enter the hollow inner lumen space of the semipermeable membrane;

the substrate medium fills the substrate containment space by traveling through the inlet tubing member into the substrate containment space;

the substrate medium envelopes the external surface side of the semipermeable membrane and permeates through the semipermeable membrane to fill the inner lumen side;

the heating member maintains a predefined temperature to maintain a predefined substrate temperature;

the agitator maintains a predefined cyclical rate;

the electric power supply coupled to the heating member;

the metabolite purifying filter member connected to the semipermeable membrane by the collection tubing member of the plurality of tubing members; and the collection reservoir connected to the metabolite purifying filter member by the collection tubing member.

8. The bioreactor of claim 7, further comprising:

a light source;

the light source contained within the sleeve; and the light source having a variable wavelength, wherein the wavelength is varied to promote metabolite production by a plurality of microorganisms contained within the hollow lumen space of the semipermeable membrane.

9. The bioreactor of claim 7, wherein the substrate medium is supplied to the substrate containment space at a predefined flow rate to permeate through the semipermeable membrane and into the hollow inner lumen space without disrupting or removing the contents therein.

* * * * *